United States Patent
Goodman

(10) Patent No.: US 12,252,451 B2
(45) Date of Patent: Mar. 18, 2025

(54) DUAL CHAMBER DISINFECTION SYSTEM

(71) Applicant: Green Logic, LLC, Takoma Park, MD (US)

(72) Inventor: Ronald N. Goodman, Rockville, MD (US)

(73) Assignee: GREEN LOGIC, LLC, Takoma Park, MD (US)

( * ) Notice: Subject to any disclaimer, the term of this patent is extended or adjusted under 35 U.S.C. 154(b) by 987 days.

(21) Appl. No.: 17/313,757

(22) Filed: May 6, 2021

(65) Prior Publication Data

US 2021/0347705 A1    Nov. 11, 2021

Related U.S. Application Data

(60) Provisional application No. 63/020,989, filed on May 6, 2020.

(51) Int. Cl.
| | | |
|---|---|---|
| C05F 17/914 | (2020.01) | |
| A61L 2/10 | (2006.01) | |
| B65G 21/00 | (2006.01) | |
| C05F 17/971 | (2020.01) | |

(52) U.S. Cl.
CPC .............. C05F 17/914 (2020.01); A61L 2/10 (2013.01); B65G 21/00 (2013.01); C05F 17/971 (2020.01); *A61L 2202/11* (2013.01)

(58) Field of Classification Search
CPC ...... C05F 17/914; C05F 17/971; B65G 21/00; A61L 2/10
See application file for complete search history.

(56) References Cited

U.S. PATENT DOCUMENTS

| | | | | |
|---|---|---|---|---|
| 6,281,001 | B1 * | 8/2001 | McNelly | C05F 17/957 |
| | | | | 210/612 |
| 2013/0157346 | A1 * | 6/2013 | Kerouac | C05F 17/70 |
| | | | | 435/267 |
| 2016/0074546 | A1 | 3/2016 | Rizzone | |

FOREIGN PATENT DOCUMENTS

| | | | | | |
|---|---|---|---|---|---|
| EP | 0962433 | A1 * | 4/1999 | | C05F 9/04 |
| EP | 3178575 | B1 | 8/2018 | | |
| KR | 20060040562 | A * | 5/2006 | | A23K 10/12 |

(Continued)

OTHER PUBLICATIONS

International Search Report and Written Opinion issued in corresponding PCT Application No. PCT/US2021/031138, issued Oct. 21, 2021.

(Continued)

*Primary Examiner* — Wayne A Langel
(74) *Attorney, Agent, or Firm* — WARNER NORCROSS + JUDD LLP

(57) ABSTRACT

A transport system can include a first chamber having a body that is configured to fully enclose a biodegradable container placed within the first chamber, the biodegradable container having food waste therein, and the biodegradable container being sealed from the ambient environment, and a disinfection system being configured to disinfect an object placed within the body. The transport system can include a second chamber having a composting system, the composting system being configured to begin to compost an object placed within the second chamber, and an enclosure that houses the first chamber and the second chamber. The first chamber, and the second chamber can be configured to be placed within a cargo space of a vehicle.

22 Claims, 5 Drawing Sheets

(56) References Cited

FOREIGN PATENT DOCUMENTS

Figure 1:
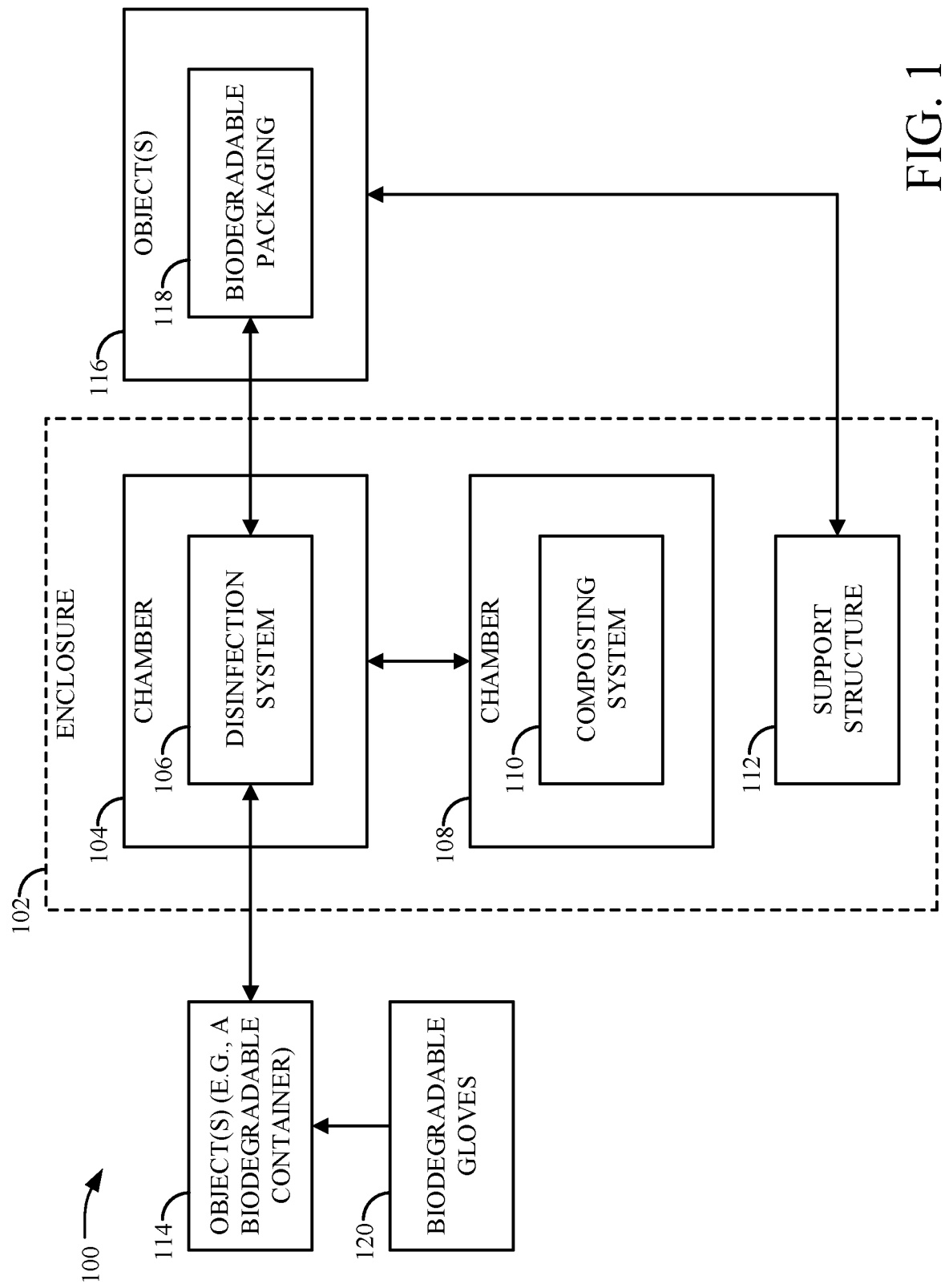

| | | | | |
|---|---|---|---|---|
| SE | 507989 C2 | * | 8/1998 | ............ C05F 17/90 |
| WO | WO-9621615 A2 | * | 7/1996 | ............ A61L 2/08 |
| WO | 2011163377 A2 | | 12/2011 | |
| WO | 2018178800 A1 | | 12/2011 | |
| WO | 2021226365 A1 | | 11/2021 | |

OTHER PUBLICATIONS

Jouhara et al., "Municipal Waste Management Systems for Domestic Use." Energy, Nov. 15, 2017, vol. 139, p. 485-506.

* cited by examiner

DUAL CHAMBER DISINFECTION SYSTEM

CROSS-REFERENCE TO RELATED APPLICATIONS

This application claims priority to U.S. Patent Application No. 63/020,989 filed May 6, 2020, and entitled, "Dual Chamber Disinfection System," which is hereby incorporated by reference in its entirety.

STATEMENT REGARDING FEDERALLY SPONSORED RESEARCH

Not Applicable.

BACKGROUND

In the food service industry (and others), suppliers must deliver products (e.g., food) to a location (e.g., restaurants, commercial establishments, residences, etc.). In addition, in some cases, other materials (e.g., food waste) must be taken away from the same location. However, these current logistics systems can be time-consuming, expensive, environmentally damaging and energy intensive (e.g., increasing the carbon footprint, adding to declining landfills and their inherent pollution, failing to recycling critical plant nutrients, and failing to add organic matter to the world's dwindling soils). Thus, it would be desirable to have improved systems and methods for transport systems.

SUMMARY OF THE DISCLOSURE

Certain embodiments of the present disclosure substantially overcome the aforementioned drawbacks by providing a novel and non-obvious transport system having at least two chambers that may be used within a vehicle to permit the delivery of food and other materials and the pick-up of waste in a single run.

Some embodiments of the disclosure provide a transport system. The transport system can include a first chamber having a body that is configured to fully enclose a biodegradable container placed within the first chamber, the biodegradable container having food waste therein, and the biodegradable container being sealed from the ambient environment, and a disinfection system being configured to disinfect an object placed within the body. The transport system can include a second chamber having a composting system, the composting system being configured to begin to compost an object placed within the second chamber, and an enclosure that houses the first chamber and the second chamber. The first chamber, and the second chamber can be configured to be placed within a cargo space of a vehicle.

In some embodiments, the biodegradable container can be remained sealed from the ambient environment for a period of time (e.g., at least twelve hours, at least one day, etc.). In some embodiments, the biodegradable container can be remained sealed during transport to the composting facility.

In some embodiments, the composting system includes a solution, or an organism that facilitates decomposition of a biodegradable object.

In some embodiments, the composting system includes the solution having the organism. The organism can be a microorganism. The microorganism can be at least one of a bacteria, a fungus, or a naturally occurring soil-borne microorganism.

In some embodiments, the composting system includes a reservoir that holds the solution that contains the organism. The reservoir can be exposed so that an object that is placed into the reservoir contacts the solution. The reservoir can be enclosed and can be in fluid communication with a conduit system that delivers the solution to an object placed within the second chamber.

In some embodiments, the composting system can include the conduit system that is in fluid communication with the reservoir. The composting system can include a nozzle in fluid communication with the reservoir and positioned within the second chamber. The nozzle can be configured to receive the solution and produce a spray of the solution that contacts an object located within the second chamber.

In some embodiments, the body of the first chamber is formed out of a rigid material. The body of the second chamber can be formed out of a rigid material that resists biodegradation by organisms that facilitate biodegradation. The first chamber can be coupled to the second chamber.

In some embodiments, the first chamber can include a door moveably coupled to the body of the first chamber. The door when closed can sealingly engage the body of the first chamber to fully enclose the object within the first chamber. When the door is opened, the interior volume of the first chamber can be accessible to remove or place and object within the interior volume.

In some embodiments, the disinfection system can include an ultraviolet (UV) light source that emits UV light within the interior volume of the first chamber.

In some embodiments, the first chamber has a plurality of sides. The disinfection system can include a plurality of UV light sources. Each UV light source can be positioned on a respective side of the plurality of sides. When an object is placed in the first chamber each of the UV light sources can surround the object. The UV light source can be part of the plurality of UV light sources.

In some embodiments, the transport system can include an object supported by a biodegradable container. After delivery of the object at a location, the biodegradable container can be configured to be placed within the second chamber. The biodegradable container can be a bag, a carton, or a box.

In some embodiments, the transport system can include biodegradable gloves configured to be worn by the operator, and placed within the second chamber after the biodegradable gloves have been worn by the operator.

Some embodiments of the disclosure provide a method of using a transport system. The method can include placing an object within a first chamber of the transport system, disinfecting the object while the object is located within the first chamber, removing the object from the first chamber, after disinfecting the object, placing a portion of the object within a second chamber of the transport system, the portion of the object being biodegradable.

In some embodiments, the method can include beginning composting the portion of the object while the portion of the object is positioned within the second chamber, emitting UV light onto the object while the object is positioned within the first chamber thereby disinfecting the object, and placing a liquid onto the portion of the object while the portion of the object is positioned within the second chamber. In some embodiments, the liquid has been seeded with microorganisms that begin the decomposition process of biodegradable materials. The microorganisms can be bacteria, fungi, or naturally occurring soil-borne microorganisms.

In some embodiments, the method can include submerging the portion of the object in the liquid. In some embodiments, the method can include spraying the portion of the object with the liquid while the portion of the object is positioned within the second chamber.

In some embodiments, the object includes a compostable container having food waste disposed therein. The method can include passing the UV light through the container that allows UV light to pass through, and subjecting the exterior of the compostable container that contains the food waste to the UV light thereby disinfecting the exterior of the compostable container.

In some embodiments, the method can include placing the entire object within a second chamber of the transport system, the entire object being biodegradable, and beginning to decompose the object while the object is positioned within the second chamber. The beginning to decompose the object can include adhering microorganisms that facilitate decomposition on the object.

In some embodiments, the method can include positioning the transport system within a cargo space of a vehicle, and removing at least one of the transport system, or the second chamber from the cargo space of the vehicle, after the second chamber has been filled past a particular level with degradable material.

In some embodiments, the method can include placing multiple bags into the second chamber, each bag being biodegradable and having food waste positioned therein, driving to a composting facility, removing each bag from the second chamber, and delivering each bag to the compositing facility.

Some embodiments of the disclosure provide a method of using a transport system. The method can include positioning the transport system within a cargo space of a vehicle, loading an object within the cargo space of the vehicle, removing the object from the cargo space of the vehicle, placing a biodegradable container having food waste therein within a chamber of the transport system, and beginning the decomposition of the biodegradable container while the biodegradable container is positioned within the chamber. The biodegradable container can be configured to be intact while the biodegradable container is positioned within the chamber of the transport system.

In some embodiments, the object is a first object, wherein the container is a first container. The method can include placing a second object within a second container of the transport system, the second object including a container that includes food waste positioned therein, disinfecting the second object while the second object is located within the second chamber, emitting UV light onto the object while the second object is positioned within the second chamber thereby disinfecting the object, removing the second object from the second chamber, after disinfecting the object; and delivering the second object to a facility that is configured to heat the food waste of the second object to generate livestock feed.

The foregoing and other aspects and advantages of the present invention will appear from the following description.

BRIEF DESCRIPTIONS FOR THE DRAWINGS

In order to assist the understanding of this invention, reference will now be made to the appended drawings, in which like reference characters refer to like elements. The drawings are exemplary only, and should not be construed as limiting the invention.

Figure 2:
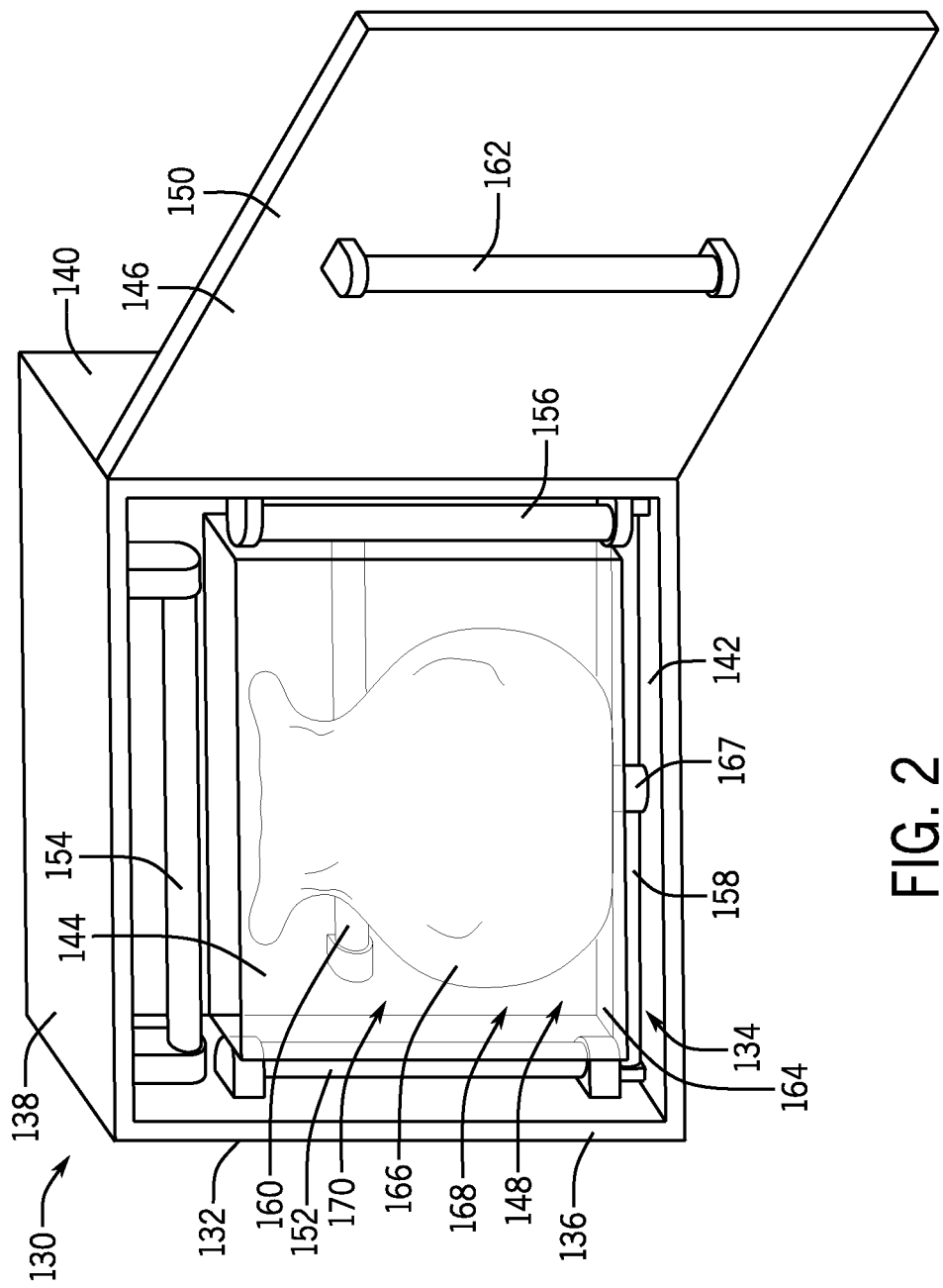
Figure 3:
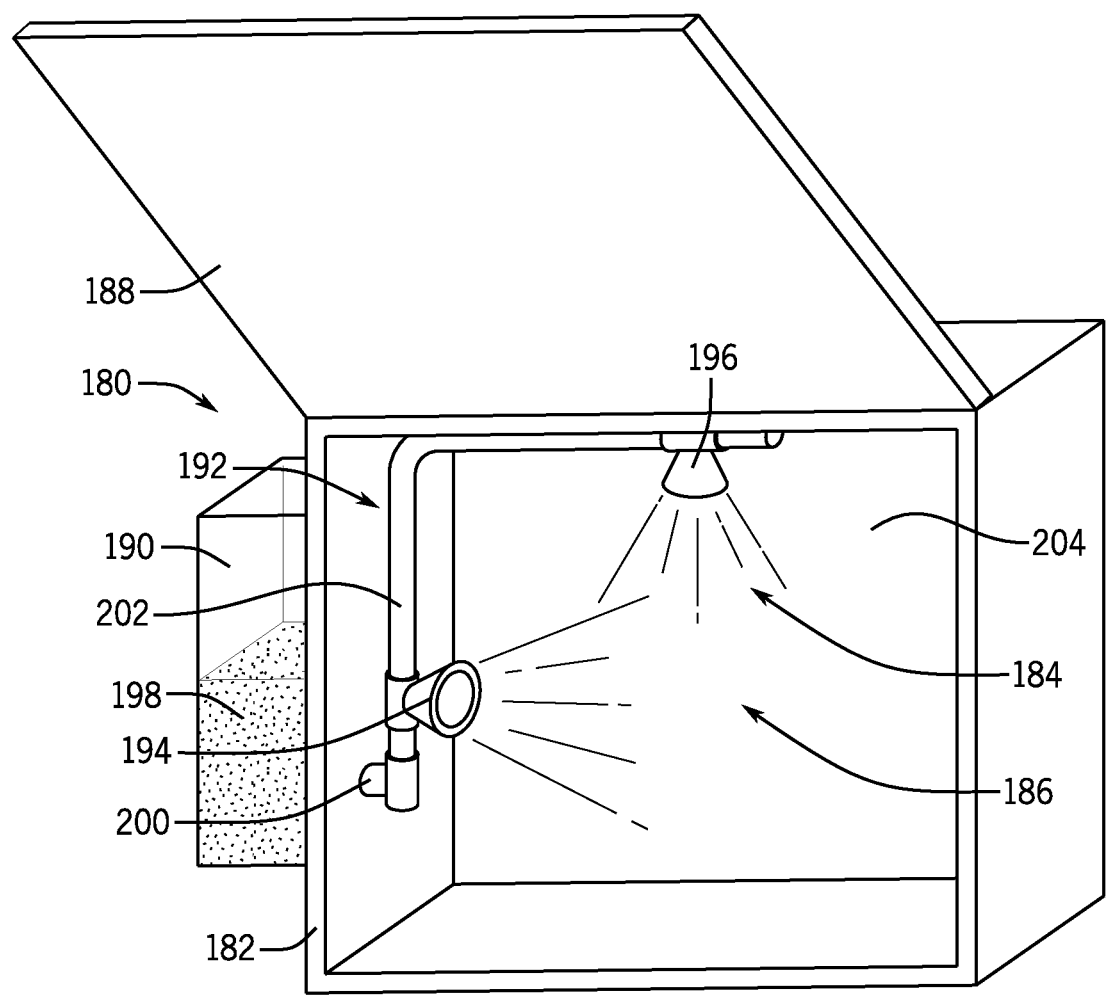
Figure 4:
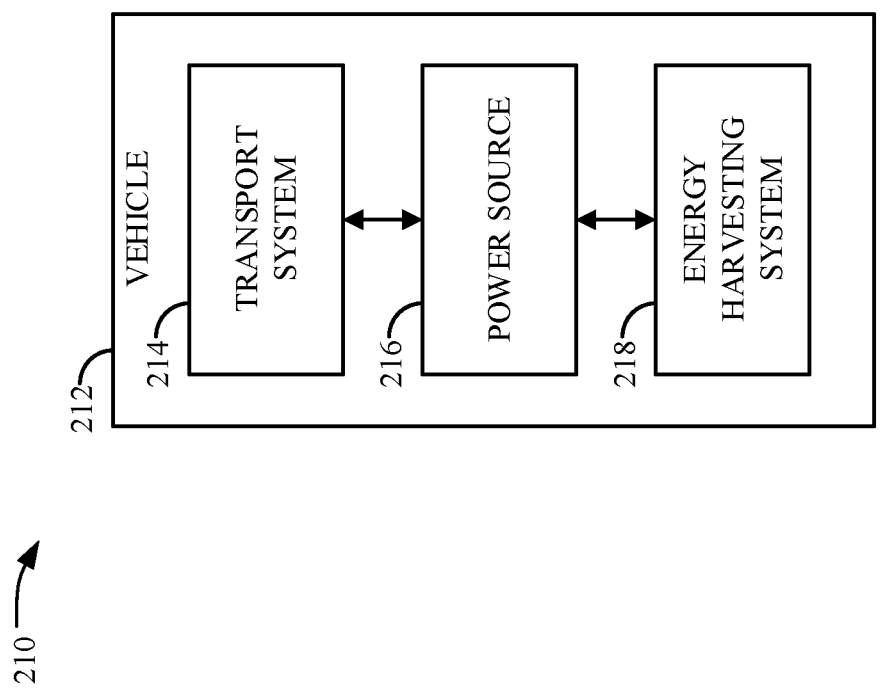
Figure 5:
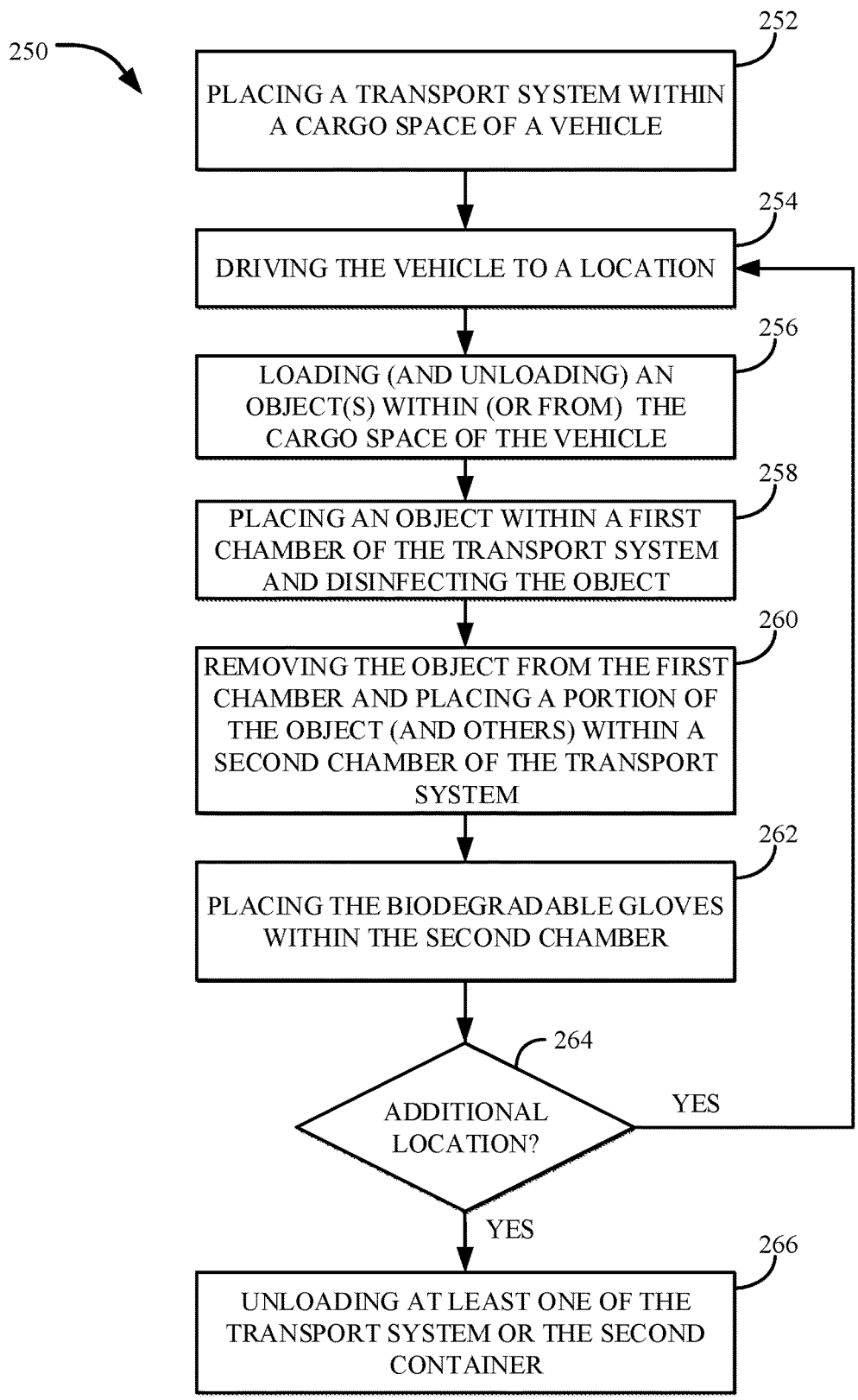

FIG. 1 is a schematic illustration of a transport system.
FIG. 2 is an illustration of a first chamber.
FIG. 3 is an illustration of a second chamber.
FIG. 4 is a schematic illustration of a vehicle system.
FIG. 5 is a flowchart of a process for using a transport system.

DETAILED DESCRIPTION

Facilities, such as restaurants, require some materials to be delivered to the facility, and others to be taken away from the facility. For example, restaurants typically require goods (e.g., food, supplies, non-food items such as bathroom supplies, and other consumables, etc.) to be brought and dropped off at the restaurant, and require other materials, such as food and non-food waste, food products (e.g., food delivery products including food made at the restaurant and packaged for delivery to a customer) to be taken away from the facility. However, current logistical practices require a driver for each service. In other words, drivers typically only deliver and drop off products at the facility, other drivers typically only take waste away from the facility, and still yet other drivers only pick-up deliverable products from the facility (e.g., food delivery drivers picking-up and delivering food delivery products).

In some cases, because it is not economically feasible to have a driver only picking up food waste (or other materials that can be recycled/composted), owners of establishments (e.g., restaurants, hotels, universities, or any commercial food service entities) typically throw away this waste in the garbage. Thus, this waste that could otherwise be recycled and composted is destined for landfills.

In some logistic configurations, a single driver is responsible for delivering products to a facility, as well as taking products (including waste) away from the facility. However, this requires the single driver to make multiple trips (e.g., at least two trips). For example, the driver must travel to the facility, deliver the products to the facility, travel back to a warehouse to deliver any remaining products back to the warehouse, travel back to the facility, pick-up the waste from the facility, and travel off-site to drop off the waste to another location (e.g., a waste disposal center). As another example, the driver must travel to the restaurant to pick-up food delivery food products, travel to the customers establishment to deliver the food products to a customer, travel back to the restaurant to pick up food waste, and travel to a different location to unload the food waste. In both of these scenarios the driver is unable to pick up the waste due to cleanliness concerns. In other words, the waste does not reside at the same location as other products for fear of cross-contamination of the products from potential disease causing microorganisms (or viruses) located within the waste. In addition, sometimes if the vehicle picks up waste from the facility (and subsequently drops off the waste), the vehicle must be cleaned prior to transporting non-waste products. Regardless, then, these current logistical scenarios (and others) require a driver to make two "runs," one to deliver deliverables (e.g., food), and the second to pick up the waste or other undesired material. These additional runs can be time-consuming, expensive, and energy intensive. In addition, these additional runs can increase the carbon footprint, add to the declining landfills including t their inherent pollution, prevent the recycling of critical plant nutrients that could otherwise be added to the world's dwindling organic matter reserves (e.g., such as within the soils).

Some embodiments of the disclosure address these issues (and others) by providing improved systems and methods for transport systems. For example, some embodiments of the disclosure provide a transport system, which can be positioned within a vehicle (e.g., the cargo space of the vehicle), and which can include a first chamber having a disinfection system, and a second chamber that includes a composting system. The disinfection system of the first chamber can disinfect the exterior surface of biodegradable containers (e.g., a biodegradable bag) that enclose waste products, such as, for example, food waste (e.g., food scraps). The composting system of the second chamber can begin to facilitate the decomposition of the biodegradable container (e.g., a compostable bag) so that when it enters the composting process (e.g., torn apart at a composting facility), the microorganisms involved in the process of composting have access to the contents of the bag. In some embodiments, the processes occurring within the second chamber can include spraying a liquid onto objects positioned within the second chamber. In addition, the second chamber can provide a location for objects to be stored while traveling, delivering products, etc., which are destined to be composted (e.g., brought to a composting facility). In this way, with the transport system positioned within the vehicle, a driver can be far more efficient in that multiple tasks can be completed in a single "run." In other words, the driver is not forced to make multiple runs, with each run completing a single task. Rather, when the driver delivers objects (e.g., bulk food products) to the facility, at the same time the driver can pick up biodegradable containers having waste positioned therein and sealed from the ambient environment (e.g., food waste). For example, the food waste within a compostable bag can be first placed in the first chamber and the disinfection system can disinfect the exterior of the compostable bag. Then, the disinfected compostable bag can be placed in the second chamber so that the composting system can begin the composing process (e.g., adhering composing microorganisms on the exterior surface of the bag), while leaving the bag intact and sealed from the ambient environment (e.g., beginning the composting process does not include creating holes in the bag), until the bag can be brought to a composting facility or a distribution hub (e.g., removed from the second chamber). In some cases, the disinfected compostable bag containing the food waste, rather than being placed within the second chamber, can be positioned within the vehicle (e.g., the cargo space of the vehicle) to be recycled as food product for livestock or composted for soil enhancement. Regardless, because the compostable bag containing the food waste has been disinfected, the bag (or other biodegradable container) can now be taken at the same time food is delivered (e.g., the compostable bag containing the food waste can occupy the same location as other delivery products without the fear of contamination). Thus, a second trip is eliminated for the driver, or in the case of multiple drivers, the delivery driver can (in addition to delivering products) take waste from the facility, which eliminates the need of the strictly waste driver (and thus saves costs, while decreasing the carbon footprint and recycling valuable soil enhancements).

In some embodiments, the driver being able to pick up food waste (e.g., in a compostable bag), at each location the driver delivers products to can be provide benefits to the driver (e.g., the wholesaler), as well as the commercial foodservice facility. For example, because the food waste taken from each location can be placed in the second chamber of the transport system, and later delivered to a composting facility, means that the food waste, rather than being recycled or worse—thrown away, is composted. In this way, less food waste can be delivered to landfills, which can decrease landfill size, decrease leaching of landfills into waterways (e.g., including pollution laden leaching), decrease cleaning of landfill areas (e.g., that cost tax payer dollars), etc. In addition, because one driver can complete multiple tasks means that less drivers are needed (e.g., reducing the carbon footprint), while simultaneously building soil and phosphate reserves (from composting).

In some cases, objects delivered to the facility include biodegradable packaging (e.g., boxes, containers, etc.) that contain the product. These biodegradable packages can be made out of a various materials, including plastics, cardboard, etc. Thus, with the inclusion of the second chamber of the transport system, this biodegradable packaging can be placed within the second chamber. In this way, the driver by using the composting system can begin to decompose the object, or to house the object while in transit to a composting facility, which is more environmentally friendly than recycling.

FIG. 1 shows a schematic illustration of a transport system 100. The transport system 100 can include an enclosure 102, a first chamber 104 having a disinfection system 106, a second chamber 108 having a composting system 110, and a support structure 112. In some cases, the enclosure 102 can house and can fully enclose the chambers 104, 108, such as when the chambers 104, 108 are not in use. For example, the enclosure 102 can be formed out of a rigid material (e.g., a metal), which can define a body of the enclosure 102. The body of the enclosure 102 can define an internal volume that can receive each of the chambers 104, 108. In some configurations, the enclosure 102 can include a door moveably coupled to the body of the enclosure 102 that can open (e.g., lifts upwardly) to allow access to the interior volume for the body. Similarly, the door can close (e.g., lowered) to seal the internal volume (and objects positioned within the interior volume, such as the chambers 104, 108) from the ambient environment. The enclosure 102 can have various shapes. For example, the enclosure 102 can be structured as a box having six sides. In some configurations, the enclosure 102 can be a frame of a vehicle, and in particular, the enclosure 102 can be a cargo space of a vehicle (e.g., a trunk, a trailer such as of a semi-truck, a refrigerated section of the vehicle, etc.)

In some embodiments, the chamber 104 can include a body that can fully enclose an object positioned within the chamber 104. For example, the body of the chamber 104 can define an internal volume that receives an object, and the internal volume can be selectively sealed from the ambient environment. As a more specific example, the chamber 104 can include a door moveably coupled to the body of the chamber 104. In this case, when the door is open, the interior volume of the chamber 104 (e.g., defined by the body of the chamber 104) is accessible to the ambient environment so that an object can be removed or placed within the internal volume of the chamber 104. Similarly, when the door is closed, the door sealingly engages with the body of the chamber 104 to seal the internal volume of the chamber 104 from the ambient environment. Similarly to the enclosure 102, the body of the chamber 104 can be formed out of a rigid material (e.g., metal), and can take on various shapes. For example, the chamber 104 can be structured as a box having six sides.

The disinfection system 106 is configured to disinfect an object that is positioned within the chamber 104 (e.g., the internal volume of the body of the chamber 104). In some configurations, the disinfection system 106 can include ultraviolet ("UV") light(s) source positioned within the body of the chamber 104. With the object positioned within the chamber 104, the UV light source can be activated (e.g., with the door of the chamber 104 closed) to deliver UV light to the object thereby disinfecting the object. In some cases, the UV light can be delivered to the object for a predetermined amount of time (e.g., at least 5 minutes, greater than 5 minutes, etc.) needed to inactive (e.g., "kill") a disease causing pathogen on the object. In some configurations, multiple sides of the body can include a UV light source. In this way, more UV light can be delivered to the object and to different surfaces of the object to disinfect the object. In some embodiments, each side of the chamber 104 can include a UV light source, so that each side of the chamber 104 can direct UV light onto the object. In this way, more UV light can be delivered to the object, and more surfaces of the object are directly exposed to the UV light. In some embodiments, each UV light source can be mounted to a respective side of the body of the chamber 104. In particular, each UV light can be mounted inside the body of the chamber 104, can be mounted outside of the body of the chamber 104, or in-between the inside and outside of the body of the chamber 104. In some cases, such as when the UV light sources are mounted outside of the chamber 104, a hole can be directed through the body of the chamber 104 to receive a portion of each UV light source. In some configurations, with the UV light sources positioned outside of the body of the chamber 104, a portion of the body adjacent each UV light source can be transparent to UV light (e.g., having a clear material, such as plastic). In this way, UV light delivered by each UV light source is transmitted through the UV transparent material and is directed into the interior volume of the chamber 104. In some embodiments, with the object positioned within the chamber 104, each UV light source surrounds the object, which can allow more UV light to be directed by the UV light sources onto the object.

Similarly to the chamber 104, the chamber 108 can also include a body that can fully enclose an object positioned within the chamber 108. For example, the body of the chamber 108 can define an internal volume that receives an object, and the internal volume can be selectively sealed from the ambient environment. As a more specific example, the chamber 108 can include a door moveably coupled to the body of the chamber 108. In this case, when the door is open, the interior volume of the chamber 108 (e.g., defined by the body of the chamber 108) is accessible to the ambient environment so that an object can be removed or placed within the internal volume of the chamber 108. Similarly, when the door is closed, the door sealingly engages with the body of the chamber 108 to seal the internal volume of the chamber 108 from the ambient environment. Similarly to the enclosure 102, the body of the chamber 108 can be formed out of a rigid material (e.g., metal), and can take on various shapes. For example, the chamber 108 can be structured as a box having six sides. In alternative configurations, however, the chamber 108 can be a bag, a container, etc. In some cases, the chamber 108 can be formed out of a rigid material that resists biodegradation.

The composting system 110 is configured to begin to decompose an object (e.g., a biodegradable object) that is positioned within the chamber 108 (e.g., the internal volume of the body of the chamber 108), and to house the object while the transport system 100 is in use (e.g., the vehicle is moving, the operator is delivering product, etc.). For example, in some cases, the object is a biodegradable object (e.g., a biodegradable carton, biodegradable bag having waste, etc.), and the biodegradable object that is placed within the chamber 108 begins to biodegrade by the composting system 110. As a more specific example, the composting system 110 can include organisms, or a solution that facilitates decomposition of a biodegradable object placed within the chamber 108. For example, the organisms can be fermentation organisms (e.g., fungi, such as yeast), microorganisms (e.g., bacteria, fungi, eukaryotes, etc.), other naturally occurring soil-borne microorganisms, etc., each of which can be located within the chamber 108 and can begin the decomposition process on objects placed therein. In some configurations, a solution can help facilitate biodegradation of the biodegradable object, which can make the biodegradable object decompose faster when it reaches a composting facility (e.g., because organisms are already adhered to the object). In some cases, as the solution (e.g., water) contacts the biodegradable object, the biodegradable object absorbs the solution and structurally weakens so that the biodegradable object can be broken up into smaller pieces thereby increasing the surface area, which better facilitates the decomposition process of the biodegradable object. However, in some cases, a biodegradable container (e.g., one having food waste therein) must stay intact (e.g., sealed from the ambient environment) during transport until delivery to a composting facility.

In some embodiments, the composting system can include a reservoir, a conduit system in fluid communication with the reservoir, and a nozzle in fluid communication with the reservoir. The reservoir can be filled with a liquid (e.g., a solution) that has been seeded with microorganisms that facilitate biodegradation of biodegradable materials, and can be positioned outside of the chamber 108 (e.g., the reservoir being coupled to the chamber 108). In some cases, after the biodegradable object has been placed within the chamber 108, a pump (not shown) can be activated to draw the solution from the reservoir and to the conduit system to be emitted through the nozzle in the form of a spray. In this way, the biodegradable object can be soaked in the liquid to begin decomposition of the biodegradable object. In some cases, the liquid can structurally weaken the biodegradable object (e.g., by being saturated in liquid and thus broken apart into smaller pieces that are more easily degraded by the microorganisms, though only when it reaches the composting facility), while, simultaneously, the microorganisms seeded into the liquid can come in contact to begin the decomposition process of the biodegradable object (e.g., which includes adhering organisms that facilitate decomposition onto an object o be decomposed).

In some embodiments, the chambers 104, 108 can be coupled to each other. In this way, the chambers 104, 108 can be moved together, such as when the transport system 100 is placed in vehicle. In some configurations, the chambers 104, 108 can be integrally formed with each other. In other configurations, the chambers 104, 108 can be separate. For example, the chamber 108 can be removably coupled to the enclosure 102 (e.g., a vehicle). In this way, the chamber 108 can be removed from the transport system 100, can be emptied of materials located within the chamber 108, and can be recoupled to the transport system 100 (e.g., the enclosure 102).

In some embodiments, such as when the enclosure 102 is a standalone structure (e.g., a container), the transport system 100 can include a support structure 112. The support structure 112 can support objects (e.g., bulk food packages, food delivery products, etc.) and prevent relative movement between the objects and the support structure 112 during travel of the transport system 100 (e.g., while in transit to a location). The support structure 112 can be implemented in different ways. For example, the support structure 112 can be a frame, a rack, a tray, etc. In some configurations, the support structure 112 can be positioned within the enclosure 102.

As shown in FIG. 1, the transport system 100 can include an object 114 to be placed in the chamber 104 and disinfected by the disinfection system 106. In some cases, the object 114 can include waste (e.g., food waste) that is placed within a biodegradable container (e.g., a biodegradable bag) whose exterior is accessible to the-UV light (e.g., the biodegradable bag could be made out of plastics, such as those made from corn, crustacean shells, etc.), and which is sealed from the ambient environment thereby enclosing the waste within the biodegradable container. Thus, the interior volume of the biodegradable container (which can include waste) can be (selectively) sealable from the ambient environment. For example, such as when the biodegradable container is a biodegradable bag, the biodegradable bag can be closed shut, such as by tying the bag (e.g., using a cable-tie, such as a zip-tie), by clipping the bag (e.g., with a clip, or other fastener), by heat sealing the bag, etc. Regardless of the configuration, the biodegradable container having waste situated therein, can be sealed from the ambient environment, which can help prevent possible leeching out of the contents within the container (e.g., including possible pathogens within the waste seeping out of the container).

In some configurations, such as when the biodegradable container is a biodegrade bag, the biodegradable bag can be at least 3 mm thick. In some cases, the object 114 can be picked up during delivery of other objects. When the object 114 is received, the object 114 can be placed within the chamber 104, and the door of the chamber 104 can be closed with the object 114 positioned therein. Then, the disinfection system 106 is activated, which can include emitting UV light at the object 114 for a predetermined period of time (e.g., a duration sufficient for inactivating or killing pathogens). After, with the object 114 disinfected, the door of the chamber 104 is opened, the object 114 is removed and is placed into the chamber 108 to begin the decomposition process by the composting system 110. In some cases, after placing the disinfected object 114 into the chamber 108, the composting system 110 can emit a liquid (seeded with microorganisms that facilitate biodegradation of objects) onto the disinfected object 114 to help facilitate the biodegradation process.

In some embodiments, the biodegradable bag can be used to transport the object 116 (e.g., the biodegradable bag can be the biodegradable packaging 118). In this way, biodegradable bag can double as a transporting configuration for the object 116, while at the same time, once the object 116 is removed, the biodegradable bag can be used and filled with waste to be subsequently placed in the chamber 108 (and began to be decomposed, and later brought to a compositing facility). In some embodiments, the biodegradable bag can also be used as biodegradable cover, weedguard, etc., in either the filled or non-filled configuration.

In some embodiments, the biodegradable container can be located within a location (e.g., a restaurant) and can be filled with compostable materials (e.g., food waste) during regular daily tasks. For example, such as when the biodegradable container is a biodegradable bag, the biodegradable bag can be dimensioned to be placed in a can (e.g., such as a trash can). Then, once the biodegradable container is filled to a particular level with biodegradable material, the biodegradable container can be sealed (e.g., the contents sealed within), which can then be picked up by a driver.

In some embodiments, the transport system 100 can include an object 116 that can include biodegradable packaging 118. For example, in some cases, the object 116 (e.g., a delivery object such as a bulk food delivery object) can be housed within (or in contact with) the biodegradable packaging 118. As a more specific example, the biodegradable packaging 118 can be a container, a box, a carton, etc., which can be formed out of a biodegradable material (e.g., paper products, cardboard, biodegradable polymers such as biodegradable plastics, etc.). In some cases, prior to delivery to a location (e.g., a restaurant, a grocery store, a warehouse, a grocery warehouse, etc.) the objects 116 can be placed within the vehicle, such as, for example, onto (or within) the support structure 112, etc. Then, in some cases, after arriving at the location and with the objects 116 having been delivered to the location (e.g., removed from the vehicle), the biodegradable packaging 118 of each object 116 can be placed either directly into the chamber 108, or can be placed into the chamber 104 (to be disinfected) before being placed into the chamber 108. In addition, while at the location, other biodegradable materials (e.g., paper products) can be collected from the location, disinfected (if desired), and placed into the chamber 108. Similarly, at this same location the object 114 can be picked up, which can be food waste within a biodegradable bag, disinfected, and placed in the chamber 106. In this way, while delivering products to the location, biodegradable waste products can be taken from the same location and recycled.

In some embodiments, the object 116 can include food delivery products (e.g., cartons or boxes of ready-made, carryout food, out of date produce, community support agriculture products, etc.) to be delivered to a customer. For example, after the driver arrives at the location, the diver can pick up the object 114 (e.g., with the gloves 120 on) and dispose of the object 114 (e.g., by placing the object 114 in the chamber 104 followed by placement into the chamber 108). Then, (or prior), the driver can load the object 116 (e.g., the food delivery product) into the vehicle (e.g., by placing the product on the support structure 112), and drive to deliver the product to the customer (e.g., a vinegar facility such as when the object is out of date produce).

In some embodiments, the transport system 100 can include biodegradable gloves 120 (or in other words compostable gloves), which can be formed out of a similar material as the biodegradable bag. The biodegradable gloves 120 (e.g., a package of 100 pairs of gloves) can be positioned within the vehicle, near the chambers 104, 108. These biodegradable gloves 120 can be worn by drivers (or other operators) prior to handling potentially pathogen laden waste materials. For example, the driver can put on (wear) the pair of biodegradable gloves 120 while placing the object 114 into the chamber 104, close the door of the chamber 104, remove the biodegradable gloves 120 and place them into the chamber 108 (e.g., to eventually be composted at a composting facility). In some cases, after placing the object 114 into the chamber 104, the operator can remove the biodegradable gloves 120 and also place them in the chamber 104 prior to closing the door of the chamber 104. Regardless, after disinfecting the object 114 (and the biodegradable gloves 120 in some cases), the object 114 (and gloves 120) can be placed in the chamber 108. In this way, by using the gloves 120, the operator does not come into direct contact with the object 114.

In some embodiments, features (and components of the chamber 108) can be incorporated with the chamber 104. For example, the chamber 104 can include a composting system 110, such as, for example, a conduit system, a reservoir filled with an inoculated liquid having organisms that facilitate biodegradation of objects, etc.

FIG. 2 shows a side isometric view of a chamber 130, which can be a specific implementation of the chamber 104.

The chamber 130 can include a body 132 and a disinfection system 134. The body 132 can include sides 136, 138, 140, 142, 144, 146, that are coupled together to define an interior volume 148 of the body 132, and that collectively enclose an object positioned therein. In some cases, the body 132 can include a door 150 that can define the side 146 of the body 132. The door 150 can be pivotably coupled to the body 132, and can be closed to sealingly engage the body 132 (e.g., via compression of a gasket) to enclose the object positioned within the interior volume 148 of the body 132 thereby isolating the object from the ambient environment. Similarly, the door 150 can be opened to allow access to the interior volume 148 of the body 132 including objects positioned therein. In some cases, the body 132 and the sides 136, 138, 140, 142, 144, 146 can be formed out of a rigid material, which does not allow UV light to pass through. For example, the body 132 can be formed out of various metals (e.g., steel).

The disinfections system 134 can include UV light sources 152, 154, 156, 158, 160, 162, each of which can be coupled to a respective side of the body 132 and disposed within the interior volume 148. For example, the UV light source 152 can be coupled to the side 136, the UV light source 154 can be coupled to the side 138, the UV light source 156 can be coupled to the side 140, the UV light source 158 can be coupled to the side 142, the UV light source 160 can be coupled to the side 144, and the UV light source 162 can be coupled to the side 146. Each of the UV light sources 152, 154, 156, 158, 160, 162 can be substantially (e.g., deviating by less than 20%) straight and can oriented in different manners. For example, the UV light source 152 can extend vertically (e.g., relative to a vertical axis of the body 132) along the side 136, the UV light source 154 can extend horizontally (e.g., relative to a horizontal axis of the body 132) along the side 138, the UV light source 156 can extend vertically along the side 140, the UV light source 158 can extend horizontally along the side 142, the UV light source 160 can extend horizontally along the side 144, and the UV light source 162 can extend vertically along the side 146. In alternative, configurations, some UV light sources can be oriented in the same manner (e.g., all the UV light sources extending vertically).

In some embodiments, the chamber 130 can include a container 164 positioned within the internal volume 148 of the body 132, and a support 167 that is coupled to the body 132 and the container 164. In some cases, the support 167 maintains the separation between the container 164 and the sides of the body 132. In some cases, although a single support 167 is shown in FIG. 2 that is coupled to the side 142 and the container 164, in alternative configurations the chamber 130 can include multiple supports, with each support coupled to a respective side of the body 132 and the container 164. As shown in FIG. 2, the container 164 is positioned so that each UV light source 152, 154, 156, 158, 160, 162 is positioned between the container 164 and the body 132 (e.g., a respective side of the body 132). In addition, the container 164 is formed out of a UV light transparent material (e.g., glass, plastic, etc.). In this way, UV light that is emitted from each UV light source 152, 154, 156, 158, 160, 162 transmits through the container 164 and is directed onto an object 166 positioned within the internal volume 168 of the container 164. The container 164 can have an opening 170 that allows access into the interior volume 168 of the container 164. The opening 170 can be aligned with the side 146 (and the door 150) so that when the door 150 is opened, the object 166 (or other objects) can be inserted through the opening 170 and placed into the internal volume 168 of the container 164.

In some cases, the interior surface of each side 136, 138, 140, 142, 144, 146 of the body 132 of the container 130 (e.g., that faces the interior volume 148) can include (e.g., can be lined with) a reflective surface (e.g., a mirrored surface), which can reflect UV light. In this way, a greater amount of UV light ca be aimed at the object positioned within the chamber 130, and additional surface can be subjected to the UV light (e.g., due to the reflecting angles of the UV light off the reflective surface). In some cases, each UV light can also have a reflective surface as well, similarly to this reflective surface.

In some cases, rather than being a container 164, the chamber 130 can include a rack that is situated within the internal volume 148. The rack can have a slot(s), a hole(s), etc., and can support the object 166 (or other objects). In this way, UV light can be emitted through the slots or holes to be directed onto the object 166. Regardless of the configuration, in some embodiments, the container 164, or the rack, does not contact any of the UV lights.

In some cases, although not shown in FIG. 2, the chamber 130 can include a power source (e.g., a power supply, such as an alternating current power outlet, an energy storage device, such as a battery) that is electrically connected to each UV light source 152, 154, 156, 158, 160, 162. In some cases, the power source can be a rechargeable battery, which can be recharged via an electrical connection to the power source of the vehicle (e.g., in which the transport system 100 is positioned). In other cases, the power source can be the power source of the vehicle (e.g., a rechargeable battery). In addition, although not shown in FIG. 2, the chamber 130 can include a computing device (e.g., a processor) in communication with each UV light sources 152, 154, 156, 158, 160, 162, and a lock. The computing device can include other typically used computing components, such as, memory, communication systems, inputs, etc. The lock can be coupled to the door 150 and the body 132 so that when the door 150 is closed and the lock is locked, the door 150 is unable to be opened. In some cases, the lock can include a sensor (e.g., a hall effect sensor, a photosensor, such as a photodiode, etc.) in communication with the computing device that can sense that the lock is in a locked position (e.g., with the door 150 closed). In this way, the computing device can cause some (or all) of the UV lights 152, 154, 156, 158, 160, 162 to emit UV light only after the door 150 is closed and the lock is locked.

In some embodiments, with the object 166 placed into the internal volume 168 of the container 164 (and supported by the container 164) and with the door 150 closed (and the lock locked), some (or all) of the UV light sources 152, 154, 156, 158, 160, 162 can begin emitting UV light at the object 166. Some (or all) of the UV light sources 152, 154, 156, 158, 160, 162 can each emit UV light for a period of time that is sufficient to disinfect the object 166 (e.g., greater than or equal to five minutes).

FIG. 3 shows a side isometric view of a chamber 180, which can be a specific implementation of the chamber 108. The chamber 180 can include a body 182 and a composting system 184. The body 182 can be structured in a similar manner as the chamber 130. For example, the body 182 can include multiple sides that together define an interior volume 186 (which collectively encloses an object positioned therein, and a door 188 that is pivotally coupled to the body 182. The door 188 can be closed to sealingly engage the body 182 to enclose the object positioned within the interior volume 186 thereby isolating the object positioned within the interior volume from the ambient environment. Similarly, the door 188 can be opened to allow access to the interior volume 186 of the body 182 including objects positioned therein. In some cases, the body 182 can be formed out of a rigid material, such as metals (e.g., steel).

As shown in FIG. 3, the composting system 184 can include a reservoir 190, a conduit system 192 in fluid communication with the reservoir 190, and nozzles 194, 196 in fluid communication with the conduit system 192. The reservoir 190 can be coupled to and can be positioned to be external to the body 182 of the chamber 180. In some cases, the reservoir 190 can be open to the ambient environment (e.g., including an opening), while in other cases, the reservoir 190 can be isolated from the ambient environment. As shown in FIG. 3, the reservoir 190 is loaded with a liquid 198 that has been seeded with organisms (e.g., microorganisms) that facilitate biodegradation of biodegradable objects positioned within the interior volume 186 of the body 182. The conduit system 192 can include conduits 200, 202, with the conduit 200 in fluid communication with the reservoir 190 and with the conduit in fluid communication with the conduit 200 and each of the nozzles 194, 196. During operation, a biodegradable object can be placed within the interior volume 186 of the body 182, the door 188 can be closed (and locked, such as the lock of the chamber 130), and a pump (not shown) can draw the liquid 198 from the reservoir 190 and direct the liquid 198 through the conduit 200, through the conduit 202, and through the nozzles 194, 196 to emit the liquid 198 (e.g., in the form of a spray) onto the object. In this way, the liquid 198 on the object begins to facilitate the composting process on the object (e.g., due to the organisms within the liquid 198). In alternative configurations, the object can be submerged partially (or fully) within the liquid 198 prior to being placed into the interior volume 186 of the body 182. In some configurations, a rear wall 204 of the body 182 can be placed on a floor (or other surface) of the vehicle the transport system 100 is positioned in. In this way, the door 188 can open upwardly (and so the liquid emitted by the nozzles does not emit upwardly).

In some embodiments, the body 182 of the chamber 180 can be formed out of, rigid, biodegradable materials (e.g., panels). For example, the body 182 can be formed out of biodegradable materials that degrade slowly (e.g., holes appear in the material after weeks, months, etc.). In this way, the chamber 180 itself can provide nourishment for the organisms positioned within the chamber 180 that facilitate decomposition, which can increase the population of the organisms. In this way, as biodegradable objects are loaded within the chamber 180, the population of organisms already present within the chamber 180 can come into contact (and adhere) to the objects. In some cases, these panels of biodegradable materials can be water rinsed of debris and left to be degraded by the organisms, and can be replaced after a particular amount of degradation has occurred. In some cases, the biodegradable material of the body 182 may inhibit the growth of pathogens (e.g., and the organisms that have been seeded by the liquid 198 within the chamber 180 can outcompete the pathogens).

FIG. 4 shows a schematic illustration of a vehicle system 210. The vehicle system 210 can include a vehicle 212, a transport system 214 (e.g., a specific implementation of the transport system 100), a power source 216, and an energy harvesting system 218. The vehicle 212 can be implemented in different ways, and thus can be a car, a truck, a trailer, etc. In some cases, the vehicle 212 can be an electric vehicle. In other cases, the vehicle 210 can be a non-food truck (e.g., which can travel to a food facility or restaurant). The power source 216 can also be implemented in different ways. For example, the power source 216 can be a rechargeable energy storage device (e.g., a battery, or battery pack) that powers a motor to drive the vehicle, and other extraneous devices of the vehicle (e.g., the radio, speaker system, etc.). In some cases, such as when the vehicle 212 is not an electric vehicle (e.g., the vehicle 212 is a fuel powered vehicle), the power source 216 can be a rechargeable energy storage device that powers only the extraneous devices of the vehicle. In some cases, the power source 216 can be a separate rechargeable battery (e.g., a lithium ion battery, a lead-acid battery, etc.) other than the batteries of the vehicle.

As shown in FIG. 4, the power source 216 is electrically connected to the transport system 214 and the energy harvesting system 218. For example, the energy harvesting system 218 can generate power and store energy within the power source 216 (e.g., when the power source 216 is implemented as an electrical energy storage device), which can then be delivered to the transport system 214. As a more specific example, the power source 216 can power the UV lights, the pumps, etc., of the transport system 214. The energy harvesting system 218 can include a turbine(s), a thermoelectric generator(s), a vibration powered generator(s), and a photovoltaic cell(s) (e.g., a solar panel). In some cases, a turbine(s) can be a wind turbine that can be coupled to an exterior of the vehicle 212. In this way, as the vehicle 212 moves, the wind turbine generates electrical energy (e.g., from the kinetic energy of the blades of the wind turbine). In some cases, a thermoelectric generator can be placed in thermal communication with a wheel of the tire of the vehicle 212 (e.g., coupled to the rim, the spokes, etc., of the wheel). In this way, the thermoelectric generator can scavenge energy from the heat-differential generated by the friction between the wheel contacting the ground. In some cases, a thermoelectric generator can be coupled to a portion of the engine (or motor, such as an electric motor) of the vehicle 212. In this way, heat generated from the engine (or motor) can be scavenged by the thermoelectric generator. In some cases, a thermoelectric generator can be coupled to a seat of the vehicle (e.g., the back rest of the seat, the headrest of the seat, the lower cushion of the seat, etc.), or other human contacting surfaces including the steering wheel. In this way, when a person sits on the seat (or contacts the steering wheel), the thermoelectric generator can scavenge heat generated by the person, which can be higher than the ambient environment within the vehicle. In some cases, a vibration powered generator can include a piezoelectric material, and can be coupled to various portions of the vehicle 212. For example, a vibration powered generator can be coupled to the driveshaft (or other moving components of the vehicle), etc. In some cases, a photovoltaic cell can be coupled to an exterior surface of the vehicle 212 (e.g., the roof of the vehicle). In this way, as the photovoltaic cell(s) are exposed to sunlight (or other lights) energy can be directed and stored by the power source 216.

FIG. 5 shows a flowchart of a process 250 for using a transport system, which can be implemented using the transport systems described herein (e.g., the transport system 100). At 252, the process 250 can include placing a transport system (e.g., the transport system 100) within a cargo space (e.g., a refrigerated section) of a vehicle (e.g., the vehicle 212). In some cases, this can include coupling the transport system 100 to a portion of the vehicle (e.g., using fasteners). In some cases, such as when the chambers of the transport system are not coupled to each other, this can include coupling a first chamber of the transport system to the vehicle (within the cargo space), and coupling a second chamber of the transport system to the vehicle (within the cargo space).

At 254, the process 250 can include driving the vehicle to a location (e.g., a facility, such as a food facility, a restaurant, etc.). In some cases, this can include driving the vehicle to the location with the transport situated within the vehicle. In some cases, prior to driving to the location, this can include loading objects to be delivered (e.g., products, such as bulk food delivery products) within the vehicle, and in particular, the cargo space of the vehicle. In some cases, this can include placing an object on a support structure of the transport system At 256, the process 250 can include loading (and unloading) an object(s) within (or from) the cargo space of the vehicle. For example, an object can be removed and delivered to the location, and an object (e.g., a food takeout object) can be taken from the location and placed within the cargo space of the vehicle (or other location of the vehicle).

At 258, the process 250 can include placing an object that includes a biodegradable material within a first chamber (e.g., the chamber 104) of the transport system and disinfecting the object (e.g., while the object is situated within the first chamber). For example, this can include opening a door of the first chamber, placing the object (e.g., a container having food waste) within the door of the first chamber, closing the door of the first chamber with the object positioned therein, locking the door (e.g., after closing the door), and emitting UV light (e.g., by turning on each UV light source) onto the object while the object is in the first chamber to disinfect the object (e.g., only after the door has been closed).

In some cases, the block 258 of the process 250 can include an operator placing a biodegradable glove on each hand, prior to handling the object to be disinfected. In this way, after the object is placed in the first chamber, but before closing the door, the operator can remove each biodegradable glove and place them in the first chamber (e.g., by inverting each glove). Then, after the door is closed (and locked), the UV lights can emit UV light to disinfect both the object and the gloves.

In some cases, the block 258 of the process 250 can include placing an object to be delivered within the first chamber, disinfecting the object to be delivered while the object is in the first chamber, removing the disinfected object from the first chamber, and delivering the disinfected object to the location.

At 260, the process 250 can include removing the object from the first chamber and placing a portion of the object (or the entire object, or a different object) that includes the biodegradable material, within the second chamber of the transport system. In some cases, this can include placing a liquid (which has been seeded with microorganisms that facilitate decomposition of biodegradable materials) onto a portion of the object while (or prior to when) the object is positioned within the second chamber. For example, this can include submerging a portion of the object into a reservoir that contains the liquid, and spraying the portion of the object with the liquid while the portion of the object is situated within the second chamber. In particular, this can include directing the liquid that is situated within the nozzles, through a conduit, and out a nozzle situated within the second chamber.

In some cases, such as when the object includes food waste, rather than placing the object into the second chamber, the object can be removed from the first chamber and placed within the cargo hold of the vehicle (or other portion of the vehicle). For example, the disinfected object can be placed on the support structure of the transport system 100. In addition, after the object has been disinfected, the food waste can be collected, and heated (e.g., cooked) to generate livestock feed (e.g., to feed pigs, for example).

In some cases, the block 260 of the process 250 can include placing a different object entirely within the second chamber. For example, this object can be biodegradable packaging, which is entirely biodegradable, such as the packaging used to transport the objects (e.g., of block 256 of the process 250). In some cases, this can include cartons, bags, boxes, which can be formed out of paper materials, or biodegradable plastics.

At 262, the process 250 can include placing the biodegradable gloves within the second chamber. For example, after the biodegradable gloves have been disinfected, the biodegradable gloves can be removed from the first chamber and placed into the second chamber.

Regardless of the configuration, after a period of time, objects that are positioned within the second chamber begin to undergo a composting process (e.g., being beginning to undergo the degradation process). In addition, the objects that are positioned within the second chamber can be isolated while the driver drives to a different location, delivers products, etc., which eventually can be brought (and delivered) to a composting location (e.g., a compositing facility).

At 264, the process 250 (e.g., a user) can determine whether there are additional locations to travel to and deliver objects to or take objects from. For example, if at 264, the process 250 determines that there are additional locations to go, the process 250 can proceed back to block 254 with the operator driving to the next location. In this case, the process 250 can include the driver driving the vehicle to the next location, unloading an object (e.g., a food delivery product) from the cargo space of the vehicle, receiving another bag of food waste, etc. In some cases, prior to disinfecting the object, but after the object is placed in the first chamber, the diver can drive to the next location. After arriving at the next location, the process 250 can include the driver disinfecting the another bag of food waste located within the first chamber, delivering an object to this location, removing the another bag of food waste from the first chamber, and placing the another bag of food waste within the second chamber. In addition, while the driver is at the next location, the process can include the driver receiving yet another bag of food waste, which can be loaded within the first chamber (e.g., without disinfecting the object), and so on. If at 264 the process 250 determines that there are no additional locations to go, the process 250 can proceed to block 264.

At 266, the process 250 can include unloading at least one of the transport system, or the second container from the cargo space of the vehicle. In addition, the block 266 of the process can include the driver driving the vehicle (and the transport system) to a composting facility, and delivering the objects positioned within the second chamber to the composting facility. For example, after the driver has completed all the stops, and at the end of the day, the driver can drive to the compositing facility, and remove the transport system, or just the second chamber. In some cases, with the second chamber removed from the vehicle, the second chamber can be emptied of its contents at the compositing facility (e.g., within a bin of at the compositing facility). In other cases, such as when the second chamber includes bags of waste (e.g., bags of food waste) a driver can remove each bag from the second chamber and deliver each bag to the compositing facility. In some embodiments, with the second chamber removed, a different second chamber (e.g., that is clean, new, etc.) can be placed onto the vehicle (e.g., the cargo space of the vehicle). In other cases, after the second chamber has been removed (and emptied), the second chamber can be placed back within the enclosure of the transport system (e.g., the vehicle). In some cases, the second chamber can be removed from the vehicle only after the second chamber has been filled past a particular level with degradable material (e.g., is more than half full). Then, a different second chamber (e.g., a second chamber that is clean, or has been cleaned) can then be placed within the vehicle.

The present disclosure has described one or more preferred embodiments, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular embodiments or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or embodiments. Further, references to particular rotational or other movements (e.g., counterclockwise rotation) is generally intended as a description only of movement relative a reference frame of a particular example of illustration.

In some embodiments, aspects of the disclosure, including computerized implementations of methods according to the disclosure, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, embodiments of the disclosure can be implemented as a set of instructions, tangibly embodied on a non-transitory computer-readable media, such that a processor device can implement the instructions based upon reading the instructions from the computer-readable media. Some embodiments of the disclosure can include (or utilize) a control device such as an automation device, a special purpose or general-purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.).

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally it should be appreciated that a carrier wave can be employed to carry computer-readable electronic data such as those used in transmitting and receiving electronic mail or in accessing a network such as the Internet or a local area network (LAN). Those skilled in the art will recognize that many modifications may be made to these configurations without departing from the scope or spirit of the claimed subject matter.

Certain operations of methods according to the disclosure, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular embodiments of the disclosure. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," etc. are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use embodiments of the disclosure. Various modifications to the illustrated examples will be readily apparent to those skilled in the art, and the generic principles herein can be applied to other examples and applications without departing from the principles disclosed herein. Thus, embodiments of the disclosure are not intended to be limited to embodiments shown, but are to be accorded the widest scope consistent with the principles and features disclosed herein and the claims below. The following detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Various features and advantages of the disclosure are set forth in the following claims.

The invention claimed is:

1. A transport system comprising:
   a first chamber having:
      a body that is configured to fully enclose a biodegradable container placed within the first chamber, the biodegradable container having food waste therein, and the biodegradable container being sealed from the ambient environment; and
      a disinfection system being configured to disinfect an object placed within the body;
   a second chamber having a composting system, the composting system being configured to begin to compost an object placed within the second chamber;
   an enclosure that houses the first chamber and the second chamber;
   a solution having an organism that facilitates decomposition of a biodegradable object;
   a reservoir that holds the solution that contains the organism, wherein the reservoir is enclosed and is in fluid communication with a conduit system that delivers the solution to an object placed within the second chamber; and
   a nozzle in fluid communication with the reservoir and positioned within the second chamber, the nozzle being configured to receive the solution and produce a spray of the solution that contacts an object located within the second chamber;
   wherein the first chamber, and the second chamber are configured to be placed within a cargo space of a vehicle.

2. The transport system of claim 1,
   wherein the body of the first chamber is formed out of a rigid material,
   wherein a body of the second chamber is formed out of a rigid material that resists biodegradation by organisms that facilitate biodegradation, and
   wherein the first chamber is coupled to the second chamber.

3. The transport system of claim 2,
   wherein the first chamber includes a door moveably coupled to the body of the first chamber, the door when closed sealingly engages the body of the first chamber to fully enclose the object within the first chamber, and
   wherein when the door is opened, the interior volume of the first chamber is accessible to remove or place and object within the interior volume.

4. The transport system of claim 1, wherein the disinfection system includes an ultraviolet (UV) light source that emits UV light within the interior volume of the first chamber.

5. The transport system of claim 4,
   wherein the first chamber has a plurality of sides,
   wherein the disinfection system includes a plurality of UV light sources, each UV light source positioned on a respective side of the plurality of sides, and
   wherein when an object is placed in the first chamber each of the UV light sources surround the object.

6. The transport system of claim 1,
   wherein the organism is a microorganism, and
   the microorganism is at least one of:
      a bacteria,
      a fungus; or
      a naturally occurring soil-borne microorganism.

7. The transport system of claim 1, further comprising an object supported by a biodegradable container, and
   wherein after delivery of the object at a location, the biodegradable container is configured to be placed within the second chamber, and
   wherein the biodegradable container is at least one of:
      a bag;
      a carton;
      or a box.

8. The transport system of claim 1, further comprising biodegradable gloves configured to be worn by the operator, and placed within the second chamber after the biodegradable gloves have been worn by the operator.

9. A method of using a transport system, the method comprising:
   placing an object within a first chamber of the transport system;
   disinfecting the object while the object is located within the first chamber;
   removing the object from the first chamber, after disinfecting the object; and
   placing a portion of the object within a second chamber of the transport system, the portion of the object being biodegradable;
   wherein the transport system is according to claim 1.

10. The method of claim 9, further comprising:
beginning composting the portion of the object while the portion of the object is positioned within the second chamber;
emitting UV light onto the object while the object is positioned within the first chamber thereby disinfecting the object; and
placing a liquid onto the portion of the object while the portion of the object is positioned within the second chamber;
wherein the liquid has been seeded with microorganisms that begin the decomposition process of biodegradable materials; and
wherein the microorganisms are at least one of:
bacteria;
fungi; or
a naturally occurring soil-borne microorganisms.

11. The method of claim 10, wherein the object includes a compostable container having food waste disposed therein, and further comprising:
passing the UV light through the compostable container that allows UV light to pass through; and
subjecting the exterior of the compostable container that contains the food waste to the UV light thereby disinfecting the exterior of the compostable container.

12. The method of claim 11, further comprising:
placing the entire object within a second chamber of the transport system, the entire object being biodegradable; and
beginning to decompose the object while the object is positioned within the second chamber;
wherein beginning to decompose the object includes adhering microorganisms that facilitate decomposition on the object.

13. The method of claim 10, further comprising:
submerging the portion of the object in the liquid; or
spraying the portion of the object with the liquid while the portion of the object is positioned within the second chamber.

14. The method of claim 9, further comprising:
positioning the transport system within a cargo space of a vehicle; and
removing at least one of the transport system, or the second chamber from the cargo space of the vehicle, after the second chamber has been filled past a particular level with degradable material.

15. The method of claim 9, further comprising:
placing multiple bags into the second chamber, each bag being biodegradable and having food waste positioned therein;
driving to a composting facility;
removing each bag from the second chamber; and
delivering each bag to the compositing facility.

16. The method of claim 9, wherein:
the body of the first chamber is formed out of a rigid material,
a body of the second chamber is formed out of a rigid material that resists biodegradation by organisms that facilitate biodegradation, and
the first chamber is coupled to the second chamber.

17. The method of claim 9, wherein:
the first chamber includes a door moveably coupled to the body of the first chamber, the door when closed sealingly engages the body of the first chamber to fully enclose the object within the first chamber, and
when the door is opened, the interior volume of the first chamber is accessible to remove or place and object within the interior volume.

18. The method of claim 9, wherein:
the first chamber has a plurality of sides,
the disinfection system includes a plurality of UV light sources, each UV light source positioned on a respective side of the plurality of sides, and
when the object is placed in the first chamber each of the UV light sources surround the object.

19. The method of claim 9, wherein:
the object is supported by a biodegradable container,
the biodegradable container is configured to be placed within the second chamber, and
the biodegradable container is at least one of: a bag; a carton; or a box.

20. The method of claim 9, wherein the transport system further includes biodegradable gloves configured to be worn by the operator, and the method includes placing the biodegradable gloves within the second chamber after the biodegradable gloves have been worn by the operator.

21. A method of using a transport system, the method comprising:
positioning the transport system within a cargo space of a vehicle; loading an object within the cargo space of the vehicle;
removing the object from the cargo space of the vehicle;
placing a biodegradable container having food waste therein within a chamber of the transport system; and
beginning the decomposition of the biodegradable container while the biodegradable container is positioned within the chamber, with the biodegradable container being configured to be intact while the biodegradable container is positioned within the chamber of the transport system;
wherein the transport system is according to claim 1.

22. The method of claim 21, wherein the object is a first object, wherein the container is a first container, and further comprising:
placing a second object within a second container of the transport system, the second object including a container that includes food waste positioned therein;
disinfecting the second object while the second object is located within the second chamber;
emitting UV light onto the object while the second object is positioned within the second chamber thereby disinfecting the object;
removing the second object from the second chamber, after disinfecting the object; and
delivering the second object to a facility that is configured to heat the food waste of the second object to generate livestock feed.

* * * * *